(12) United States Patent
Kravitz et al.

(10) Patent No.: US 7,132,054 B1
(45) Date of Patent: Nov. 7, 2006

(54) METHOD TO FABRICATE HOLLOW MICRONEEDLE ARRAYS

(75) Inventors: Stanley H. Kravitz, Placitas, NM (US); David Ingersoll, Albuquerque, NM (US); Carrie Schmidt, Los Lunas, NM (US); Jeb Flemming, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 279 days.

(21) Appl. No.: 10/936,360

(22) Filed: Sep. 8, 2004

(51) Int. Cl.
*C03C 25/00* (2006.01)
*C03C 25/68* (2006.01)
*B81C 1/00* (2006.01)

(52) U.S. Cl. .......................... 216/11; 216/39; 216/41; 216/49; 216/55; 216/56; 216/87; 216/97; 65/472; 65/31; 65/33.2; 65/33.7; 430/320

(58) Field of Classification Search .................. None
See application file for complete search history.

(56) References Cited

U.S. PATENT DOCUMENTS

| | | | |
|---|---|---|---|
| 4,444,616 A * | 4/1984 | Fujita et al. ............. 216/87 |
| 6,312,612 B1 * | 11/2001 | Sherman et al. .......... 216/2 |
| 6,503,231 B1 * | 1/2003 | Prausnitz et al. ........ 604/272 |
| 6,749,792 B1 | 6/2004 | Olson |
| 6,783,920 B1 * | 8/2004 | Livingston et al. ...... 430/322 |
| 6,790,372 B1 * | 9/2004 | Roy et al. ............... 216/10 |
| 6,932,933 B1 * | 8/2005 | Helvajian et al. ........ 264/482 |
| 2004/0063100 A1 * | 4/2004 | Wang .......................... 435/6 |
| 2004/0186419 A1 * | 9/2004 | Cho ........................... 604/22 |
| 2004/0267205 A1 * | 12/2004 | Stemme et al. .......... 604/173 |
| 2005/0011858 A1 * | 1/2005 | Kuo et al. ................ 216/17 |
| 2005/0171480 A1 * | 8/2005 | Mukerjee et al. ........ 604/173 |
| 2006/0015061 A1 * | 1/2006 | Kuo et al. ................ 604/47 |
| 2006/0084942 A1 * | 4/2006 | Kim et al. ............... 604/890.1 |

FOREIGN PATENT DOCUMENTS

JP 61006143 A * 1/1986

OTHER PUBLICATIONS

Fuqua, P. et al "Fabrication of True 3D Microstructures in Glass/Ceramic Materials by Pulsed UV Laswer Volumetric Exposure Techniques" SPIE vol. 3618, Jan. 1999, 213-220.*
Cheng, Y. et al "3D microstructuring inside photosensitive glass by use of a femtosecond laser for lab.-on-chip applications" SPIE, vol. 4977, 2003, 314-323.*
Dietrich, T.R. et al "Photoetchable glass for microsystems: tips for atomic force microscopy". Micromech. Microeng. vol. 3, 1993, 187-189.*
Khumpuang, S. et al "Fabrication and simulation of novel crown-chaped microneedle array" SPIE, vol. 5651, 2005, 288-297.*
Hansen, W. W. et al "Direct-Write UV Laser Microfabrication of 3D Structures in Lithium-Alumosilicate Glass" SPIE, vol. 2991, 1997, 104-112.*

(Continued)

*Primary Examiner*—Anita Alanko
(74) *Attorney, Agent, or Firm*—Kevin W. Bieg

(57) ABSTRACT

An inexpensive and rapid method for fabricating arrays of hollow microneedles uses a photoetchable glass. Furthermore, the glass hollow microneedle array can be used to form a negative mold for replicating microneedles in biocompatible polymers or metals. These microneedle arrays can be used to extract fluids from plants or animals. Glucose transport through these hollow microneedles arrays has been found to be orders of magnitude more rapid than natural diffusion.

28 Claims, 8 Drawing Sheets

OTHER PUBLICATIONS

Zhang, "Micromachined Needles for Microbiological Sample and Drug Delivery System," Proceedings of ICMENS2003: The 2003 International Conference on MEMS, NANO, and Smart Systems, Jul. 20-23, 2003 in Banff, Alberta-Canada.

Gardeniers, "Silicon Micromachined Hollow Microneedles for Transderman Liquid Transport," Journal of Microelectromechanical Systems, vol. 12, No. 6, Dec. 2003, 855-862.

Griss, "Side-Opened Out-of-Plane Microneedles for Microfluidic Transdermal Liquid Transfer," Journal of Microelectromechanical Systems, vol. 12, No. 3, Jun. 2003, 296-301.

Prausnitz, "Microneedles for transdermal drug delivery," Elsevier, Advanced Drug Delivery Reviews, 56, 2004, 581-587.

Tan, "Novel low cost fabrication of microneedle arrays for drug delivery applications," Proceedings of SPIE, vol. 4936 (2002) 113-118.

Dietrich, "Fabrication technologies for microsystems utilizing photoetchable glass," Microelectronic Engineering 30 (1996) 497-504.

Mrotzek, "Processing techniques for photostructurable glasses," Glass Sci. Technol. 76 (2003) No. 1, 22-27.

Dietrich, "FOTURAN photo-etchable glass," SCHOTT glass made of ideas, http://www.us.schott.com/tgd/english/products/foturan.html, no date.

* cited by examiner

METHOD TO FABRICATE HOLLOW MICRONEEDLE ARRAYS

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to a method to fabricate hollow microneedle arrays and, in particular, a method to fabricate hollow microneedle arrays using a photoetchable glass wafer.

BACKGROUND OF THE INVENTION

Hollow microneedle arrays are being developed for transdermal drug delivery and the withdrawal of body fluids for biomedical and other applications. The hollow microneedle array can provide a minimally invasive means to transport relatively large molecules into and out of the skin. Microneedles are desirable because their small size and extremely sharp tip reduces insertion pain and tissue trauma to the patient. The length of the microneedles can be kept short enough to not penetrate to the pain receptors in the inner layers of the skin. Furthermore, the bore of the hollow microneedles can be large enough to provide a relatively rapid rate of drug delivery or withdrawal of bodily fluid. For drug delivery, the use of micron-size needle arrays increases skin permeability due to the needle's penetration of the outer layer of the skin, enabling the drugs to enter the body at therapeutically useful rates. Likewise, hollow microneedle arrays may replace painful hypodermic needles or syringes used for the sampling of biological fluids (e.g., blood or interstitial fluid). For example, for diabetics it is necessary to monitor and control blood sugar levels during the course of a day. The most common approach to monitor blood sugar is to stick the finger with a small needle and measure sugar level in the blood drop that forms at the site of the needle-stick. As a result, the patient may become sensitized to the frequent, painful needle-sticks, perhaps to the point of avoidance, and the sampling protocol is problematic. Microneedle arrays may enable the diabetic to routinely sample blood sugar levels in a pain-free manner.

With out-of-plane microneedles, the longitudinal axis of the microneedles is perpendicular to the wafer. These microneedles are typically short (e.g., less than a few hundred microns) and only penetrate the outer barrier layers of the skin. Out-of-plane needles can typically be made with a large density of needles per chip. Therefore, two-dimensional arrays of microneedles have been used to obtain adequate fluid flow at reasonable pumping rates. See, e.g., P. Zhang et al., "Micromachined Needles for Microbiological Sample and Drug Delivery System," *Proc. Intl. Conf. MEMS, NANO, and Smart Systems (ICMENS'03)*, Jul. 20–23, 2003, Banff, Alberta, Canada. However, only microneedles with the correct geometry and physical properties can be inserted into the skin. In particular, the safety margin for needle breakage, or the ratio of microneedle fracture force to skin insertion force, has been found to be optimum for needles having a small tip radius and large wall thickness. See M. R. Prausnitz, "Microneedles for transdermal drug delivery," *Advanced Drug Delivery Reviews* 56, 581 (2004).

Microneedle arrays have been fabricated by a number of micromachining processes. Out-of-plane microneedles have typically been fabricated using bulk micromachining or LIGA techniques (LIGA is the German acronym for X-ray lithography, electrodeposition, and molding). Therefore, most of these microneedles have been made of silicon or metals. Silicon bulk micromachining has used either deep reactive ion etching (DRIE) alone or in combination with KOH etching to form the hollow microneedles. See H. J. G. E. Gardeniers et al., "Silicon Micromachined Hollow Microneedles for Transdermal Liquid Transport," *J. Microelectromechanical Systems* 12(6), 855 (2003) and P. Griss et al., "Side-Opened Out-of-Plane Microneedles for Microfluidic Transdermal Liquid Transfer," *J. Microelectromechanical Systems* 12(3), 296 (2003). However, these fabrication processes are long and difficult and can result in inconsistent wall slopes both in inside diameter and outside diameter of the hollow microneedles. Furthermore, the expensive capital equipment required is slow and not well-suited to eventual mass production of microneedles. Finally, at the end of the process, the silicon microneedles require oxidation so that only a biocompatible silicon dioxide surface is in contact with biological processes.

Therefore, a simple fabrication process using inexpensive equipment, providing repeatable results, and directly producing hollow microneedles in a biocompatible substrate is needed. The present invention provides a method to fabricate hollow microneedle arrays using a photoetchable glass wafer that solves these problems.

SUMMARY OF THE INVENTION

The present invention is directed to a method to fabricate a hollow microneedle array, comprising exposing a photoetchable glass wafer to ultraviolet light through a patterned mask to define a latent image of a bore of at least one hollow microneedle in the glass wafer; heating the glass wafer to a temperature in excess of the glass transformation temperature to transform the amorphous material in the exposed latent image of the bore of the at least one microneedle to a crystalline material, thereby providing a crystallized image of the bore of the at least one microneedle in the glass wafer; exposing the glass wafer to ultraviolet light through a patterned mask to define a latent image of the regions between the at least one hollow microneedle; heating the glass wafer to a temperature in excess of the glass transformation temperature to transform the amorphous material in the exposed latent image of the between regions to a crystalline material, thereby providing a crystallized image of the between regions in the glass wafer; and etching the glass wafer in an etchant to remove the crystallized image regions, thereby providing a glass hollow microneedle array comprising the at least one hollow microneedle. Alternatively, both exposures can be done sequentially, followed by a single heat treatment, and etching.

The method can further comprise depositing a mold material onto the glass hollow microneedle array to provide a negative mold, removing the negative mold from the glass hollow microneedle array, casting a liquid polymer onto the negative mold, solidifying the polymer in the negative mold, and removing the solidified polymer from the negative mold to provide a polymeric hollow microneedle array.

Alternatively, a negative mold can be made directly from the photoetchable glass, a structural material can be molded into the glass negative mold, and the negative mold can be removed to provide a microneedle array of the structural material.

The photoetchable glass preferably comprises Foturan® glass. Using Foturan® glass, an array of hollow microneedles can be fabricated using inexpensive equipment commonly found in semiconductor fabrication facilities, including a UV light source, wet chemical baths, ovens, and inexpensive lapping equipment. The rapid turn-around of the fabrication method enables easy process development, since optimization of process parameters can be quickly effected. Finally, the glass is inert to biological fluids and is already used in PCR replication activities. Transport of fluids through a glass hollow microneedle array has been demonstrated at 500 times greater than natural diffusion.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1A:
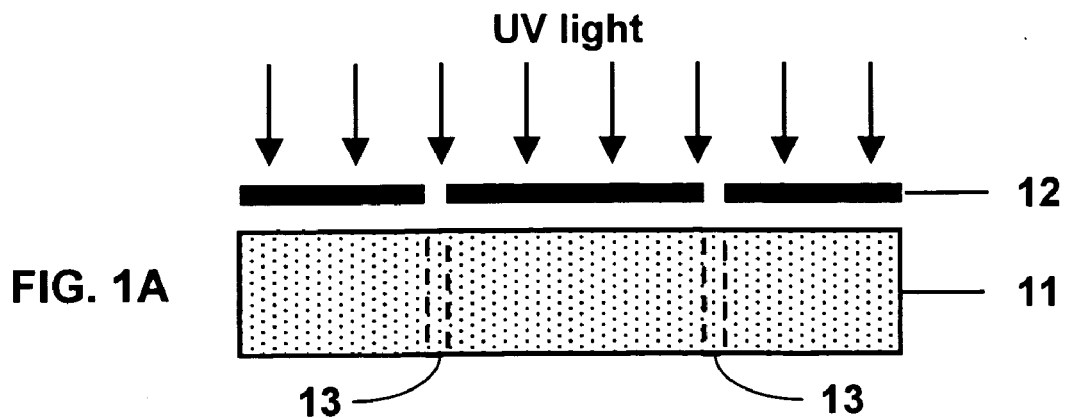
FIGS. 1A–1E show a schematic illustration of a method to fabricate a glass hollow microneedle array using a photoetchable glass wafer.

Photoetchable glasses have several advantages for the fabrication of a wide variety of Microsystems components. High-aspect-ratio microstructures can be mass produced relatively inexpensively with these glasses using conventional semiconductor processing equipment. Glasses have high temperature stability, good mechanical properties, are electrically insulating, and have better chemical resistant than plastics and many metals. A particularly attractive photoetchable glass is Foturan®, made by Schott Corporation and imported into the U.S. by Invenios Inc. Foturan® comprises a lithium-aluminum-silicate glass containing traces of silver and germanium ions. When exposed to UV-light within the absorption band of the metal ion dopants in the glass, the germanium acts as a sensitizer, absorbing a photon and stripping an electron that reduces neighboring silver ions to form colloidal silver atoms. These silver colloids provide nucleation sites for crystallization of the surrounding glass. If exposed to UV light through a mask, only the exposed regions of the glass will crystallize during subsequent heat treatment at a temperature greater than the glass transformation temperature (e.g., greater than 450° C. in air for Foturan®). These nucleated lithium metasilicate crystals typically have diameters of 1–10 microns. The crystalline phase is more soluble in hydrofluoric acid (HF) than the unexposed vitreous, amorphous regions. In particular, the crystalline regions are preferentially etched about 20 times faster than the amorphous regions in 10% HF, enabling microstructures with aspect ratios of about 20:1 to be formed when the exposed regions are removed. Therefore, this process can produce holes of greater than about 25 microns with a sidewall slope of about 1–4°. See T. R. Dietrich et al., "Fabrication technologies for microsystems utilizing photoetchable glass," *Microelectronic Engineering* 30, 497 (1996), which is incorporated herein by reference.

In FIGS. 1A–1E is shown a schematic illustration of a preferred method to fabricate a hollow microneedle array, comprising at least one hollow microneedle, using a photoetchable glass wafer. The preferred method comprises exposing the photoetchable glass wafer to ultraviolet light through a patterned mask to define a latent image of a bore of at least one hollow microneedle in the glass wafer; heating the glass wafer to a temperature in excess of the glass transformation temperature to transform the amorphous material in the latent image of the exposed bore of the at least one microneedle to a crystalline material, thereby providing an crystallized image of the bore of the at least one microneedle in the glass wafer; exposing the glass wafer to ultraviolet light through a patterned mask to define a latent image of the regions between the at least one hollow microneedle; heating the glass wafer to a temperature in excess of the glass transformation temperature to transform the amorphous material in the exposed latent image of the between regions to a crystalline material, thereby providing a crystallized image of the between regions in the glass wafer; and etching the glass wafer in an etchant to remove the crystallized image regions, thereby providing a glass hollow microneedle array comprising the at least one hollow microneedle.

In FIG. 1A, a thick photoetchable glass wafer 11 is exposed to deep UV light through a hard lithography mask 12 to define a latent image 13 of the bore of the at least one hollow microneedle. The photoetchable glass wafer 11 preferably comprises Foturan® Microglass (Invenios, Inc). The wavelength of the UV light preferably corresponds to the absorption band for the sensitizing ion dopant dispersed in the glass. The energy density of the UV light and the exposure time are preferably sufficient to expose the latent image 13 through the thickness of the wafer 11. For processing hollow microneedles, a deep UV light source (e.g., available from ABM Corp.) can be used and the intensity of the light source at a wavelength of 240 nm can be about 16.5 mw/cm$^2$. To define a latent image 13 of the bore through the entire thickness of a 1 mm Foturan® wafer at this wavelength and intensity, the exposure time can be about 4 hours. Using a more intense light source can shorten the exposure time. The mask 12 can be a fused silica photolithography mask, which blocks the deep UV light in the unopen portions of the mask. The openings in the mask preferably define at least one circular bore-hole, although other cross-sections can also be used. The bores are preferable small enough to provide a microneedle that easily penetrates the skin, yet also large enough to enable adequate fluid flow. The diameter of the circular bore-holes is preferably greater than 25 microns and, more preferably, greater than 100 microns.

Figure 1B:
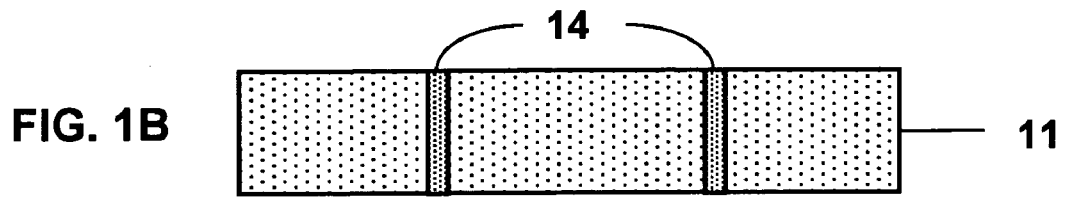

In FIG. 1B, the exposed Foturan® wafer 11 is heat treated at a temperature greater than the glass transformation temperature for a time duration sufficient to convert the exposed amorphous latent image regions to the crystalline phase. The exposed Foturan® glass wafer can be heat treated at 600° C. for 1 hour. This heat treatment converts the amorphous-phase latent image regions to crystalline-phase image regions 14 that can be etched later to form the through-hole bores 18 of the hollow microneedles 19.

Figure 1C:
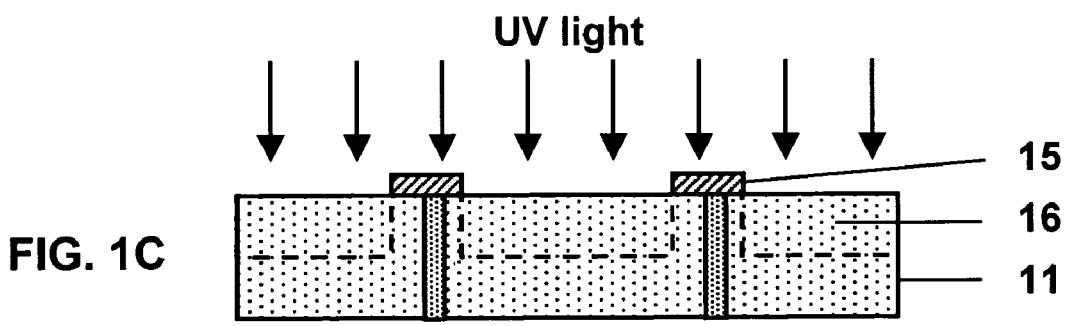

In FIG. 1C, when heat-treating is completed, a negative acting photoresist (e.g., JSR Microposit) 15 is patterned onto the front side of the Foturan® glass wafer using the darkened crystalline image 14 as a reference. The photoresist mask 15 blocks the areas that will form the walls of the hollow microneedles from exposure to the deep-UV light. Therefore, the UV exposure defines a latent image 16 of the region between the microneedles that are to be removed by etching. If the tip is too small, the microneedle may shear upon insertion into the skin. Furthermore, the wall thickness of the body of the microneedle at the tip is preferably about 50 microns or greater. If the tip is too large, the microneedle will not penetrate the skin. The photoresist pattern preferably provides a circular microneedle, after etching, having a tip diameter of greater than 100 microns and, preferably, less than 300 microns. Other microneedle tip cross-sections and dimensions can be used. The photoresist mask 15 can be patterned so that the bore 18 is offset from the tip of the microneedle 19, thereby reducing clogging of the bore which can occur when the fluid outlet is at the tip of the needle. The photoresist-masked glass wafer 11 is then exposed again to the deep-UV light for a sufficient period of time to define the height of the microneedles. For example, for 400–500 micron tall microneedles in Foturan®, the second exposure can be 35 minutes using the UV light source described above.

Figure 1D:
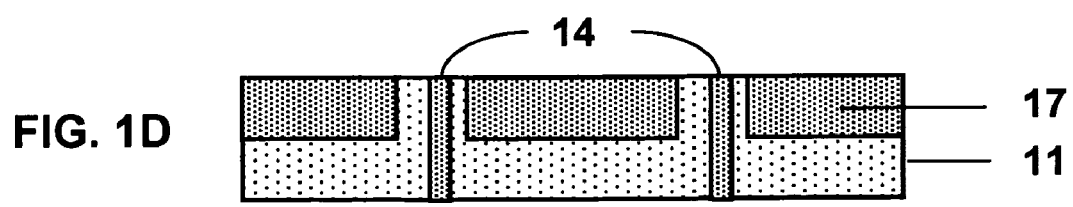

In FIG. 1D, the exposed glass wafer 11 can be cleaned of the photoresist and heat treated to crystallize the latent image 16 defined by the second exposure. Heat treatment of the twice-exposed Foturan® for an additional 1 hour at 600° C. will form crystallized image regions 17 between the microneedles, in addition to the previously formed crystallized images 14 of the bores. The surface of the wafer can be lapped.

Figure 1E:
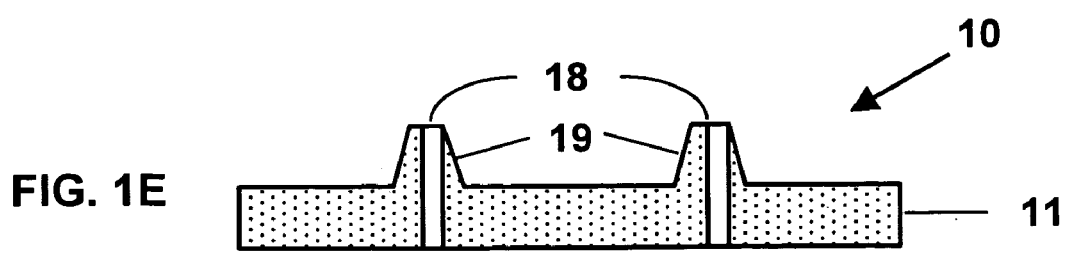

In FIG. 1E, the glass wafer 11 is etched to remove the crystallized image regions 14 to form the bores 18 and to remove the crystallized image regions 17 to form the spacings between the hollow microneedles 19. The backside of the wafer can be covered with photoresist (not shown) to prevent etching of the wafer backside. The Foturan® glass wafer can be etched for 40 minutes in unbuffered 10:1 HF solution. The crystalline material preferentially etches 20:1 times faster then the vitreous material in a 10:1 HF solution, using an ultrasonic bath. Since the wet chemical etch is anisotropic, an array of hollow microneedles 10 with sloped sidewalls and a small tip radius is formed, as is preferred for penetration of the skin. The etching time can be adjusted to obtain the desired microneedle height and cross-sectional dimensions.

Alternatively, both UV exposures can be done sequentially to define the latent images of the regions between the microneedles and the bores, followed by a single heat treatment, albeit while sacrificing mask alignment accuracy. For example, a first exposure of the regions between the microneedles can produce enough darkening by itself (apparently due to the formation of isolated silver atoms) to enable alignment of the bore mask to the faintly darkened latent image 16 of the between regions. Following a second exposure to define the latent image 13 of the bores, the exposed wafer can be heat treated to crystallize both latent images 16 and 13 simultaneously to form crystallized images of both the between regions 17 and the bores 14. The crystallized images can then be etched to form the glass hollow microneedle array. Alternatively, the bores can be defined in a first exposure and the between region mask aligned to the darkened latent image of the bores for a second exposure of the between regions, followed by a single heat treatment.

Figure 2:
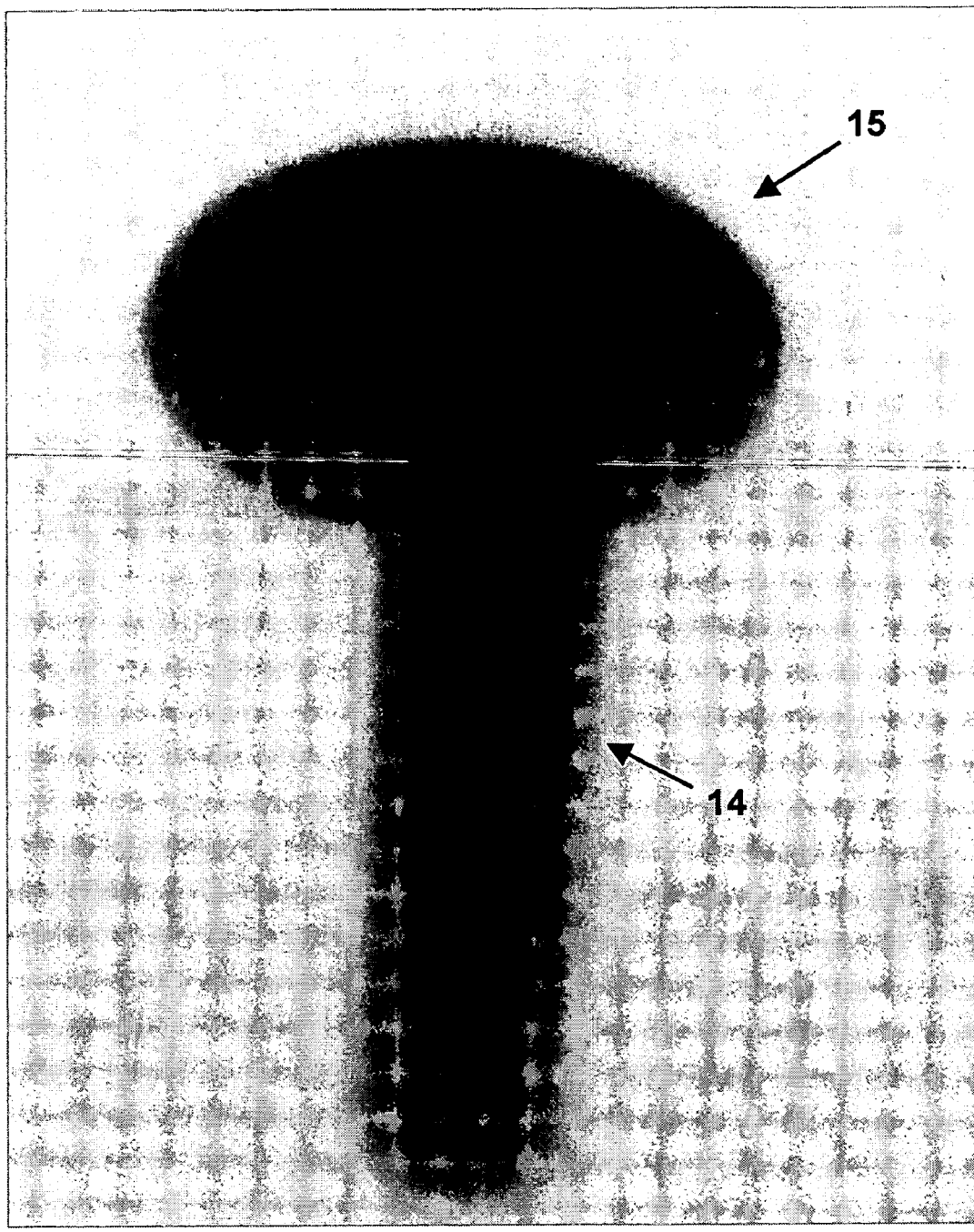
FIG. 2 shows a bottomside view photograph of a heat-treated image of a round bore and a circular patterned photoresist on the topside of a transparent Foturan® glass wafer after a first exposure to UV light.

In FIG. 2 is shown a bottomside view photograph of a dark-shaded, crystallized image 14 of a circular bore and a circular patterned photoresist 15 on the topside of a transparent Foturan® glass wafer after a first exposure to UV light and a first heat treatment, but before the second exposure, according to the preferred method shown in FIGS. 1A and 1B.

Figure 3:
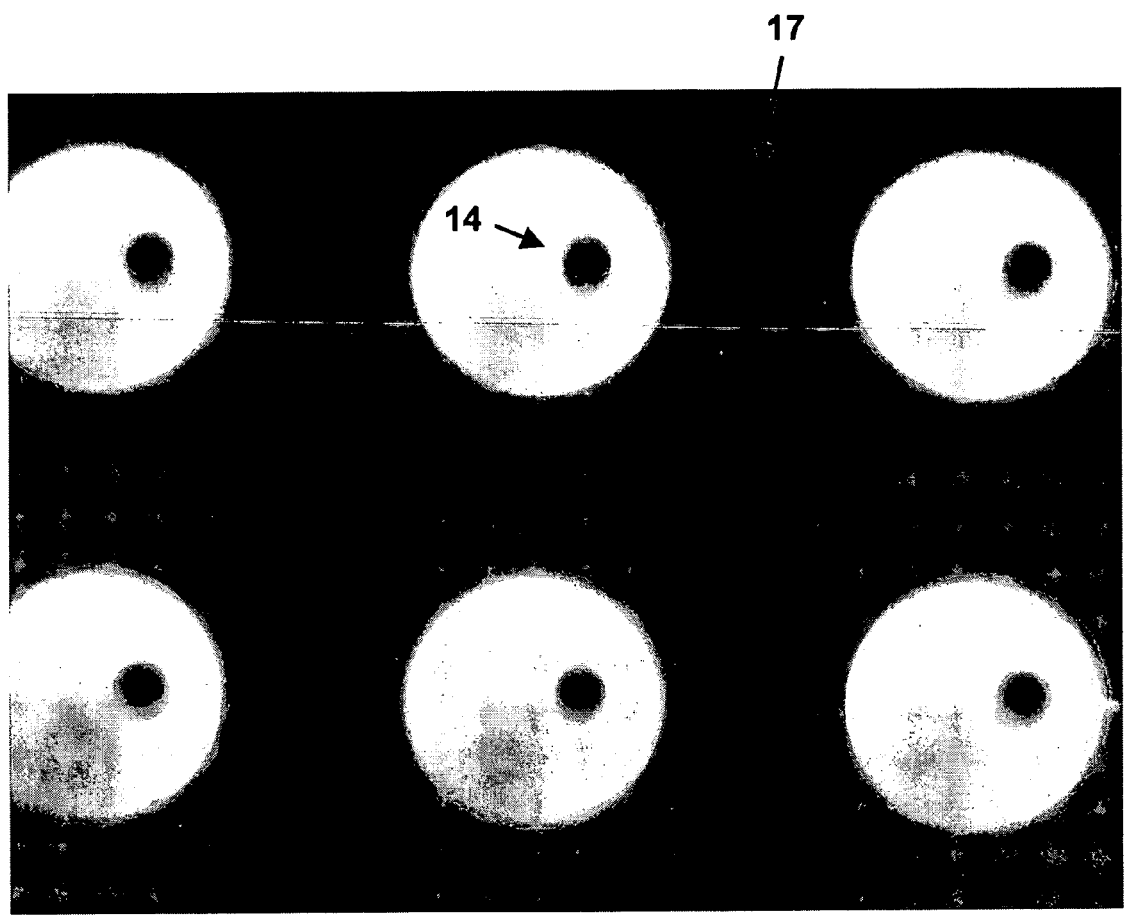
FIG. 3 shows a topside view photograph of heat-treated images of the regions between the microneedles and the round bores of a glass microneedle array after a second exposure to UV light.

In FIG. 3 is shown a topside view photograph of the dark-shaded, crystallized image 17 the spacings between the outsides of the microneedles in an array, in addition to the previously formed dark-shaded crystallized images 14 of the circular bores, after a second exposure to UV light and a second heat treatment, but before etching, according to the preferred method shown in FIGS. 1A to 1D. The light-shaded regions surrounding each dark-shaded bore corresponds to the unexposed vitreous regions underneath the patterned photoresist 15 in FIG. 2. The center-to-center spacing of the light-shaded vitreous regions is about 1 mm. Each light-shaded vitreous region has a diameter of about 350 microns, before etching. The diameter of each exposed, dark-shaded bore region is about 50 microns, before etching. The bores are offset from the center of the microneedle tip by about 50 microns.

Figure 4:
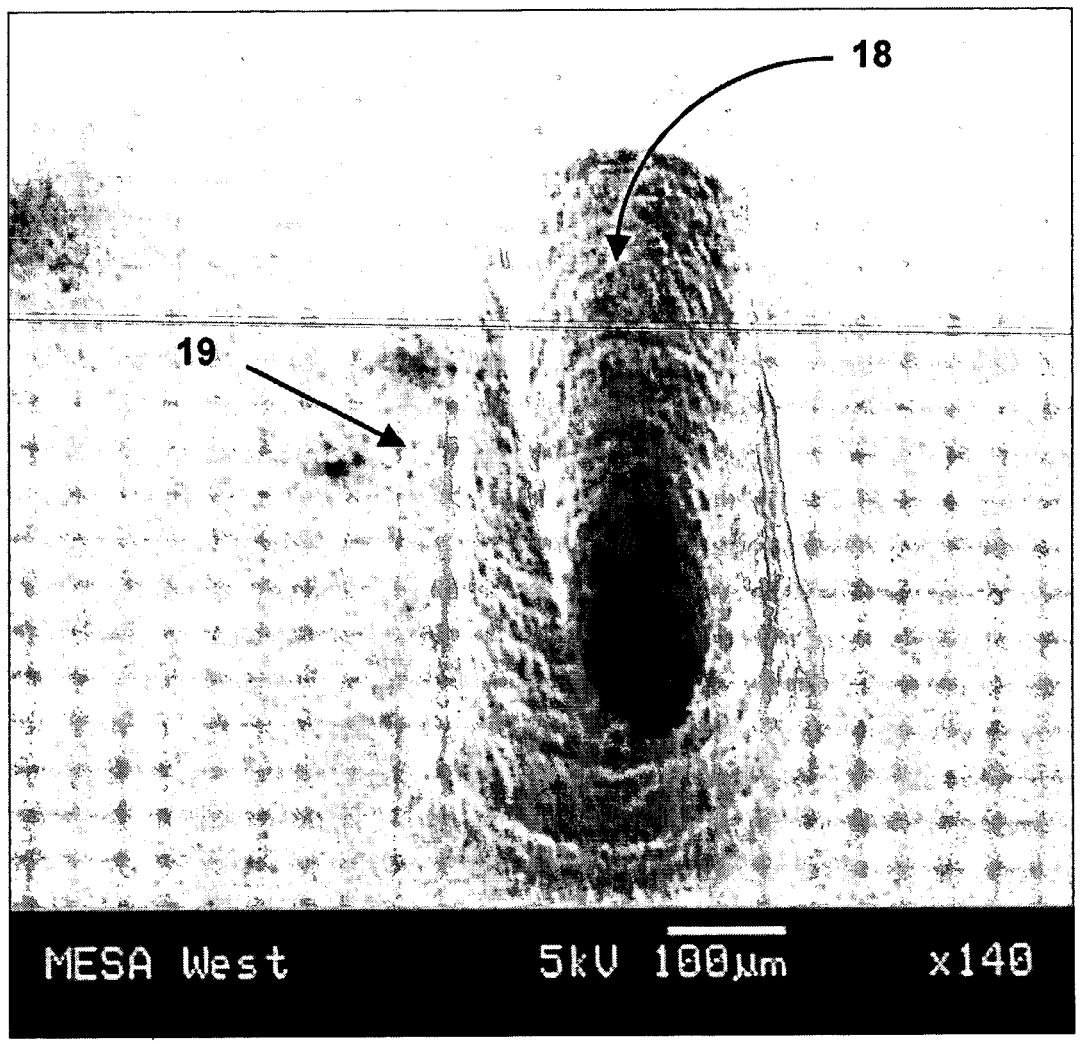
FIG. 4 shows a scanning electron micrograph (SEM) of a single glass hollow tapered microneedle.

In FIG. 4 is shown a scanning electron micrograph (SEM) of a single glass hollow microneedle 19, after etching. The microneedle is about 400–500 micrometers tall with through-holes 18 that are 1 mm deep. The outside diameter of the tapered microneedle 19 at the base is about 350 microns and about 200 microns at the tip. The diameter of the offset bore 18 at the microneedle tip is about 200 microns.

Figure 5:
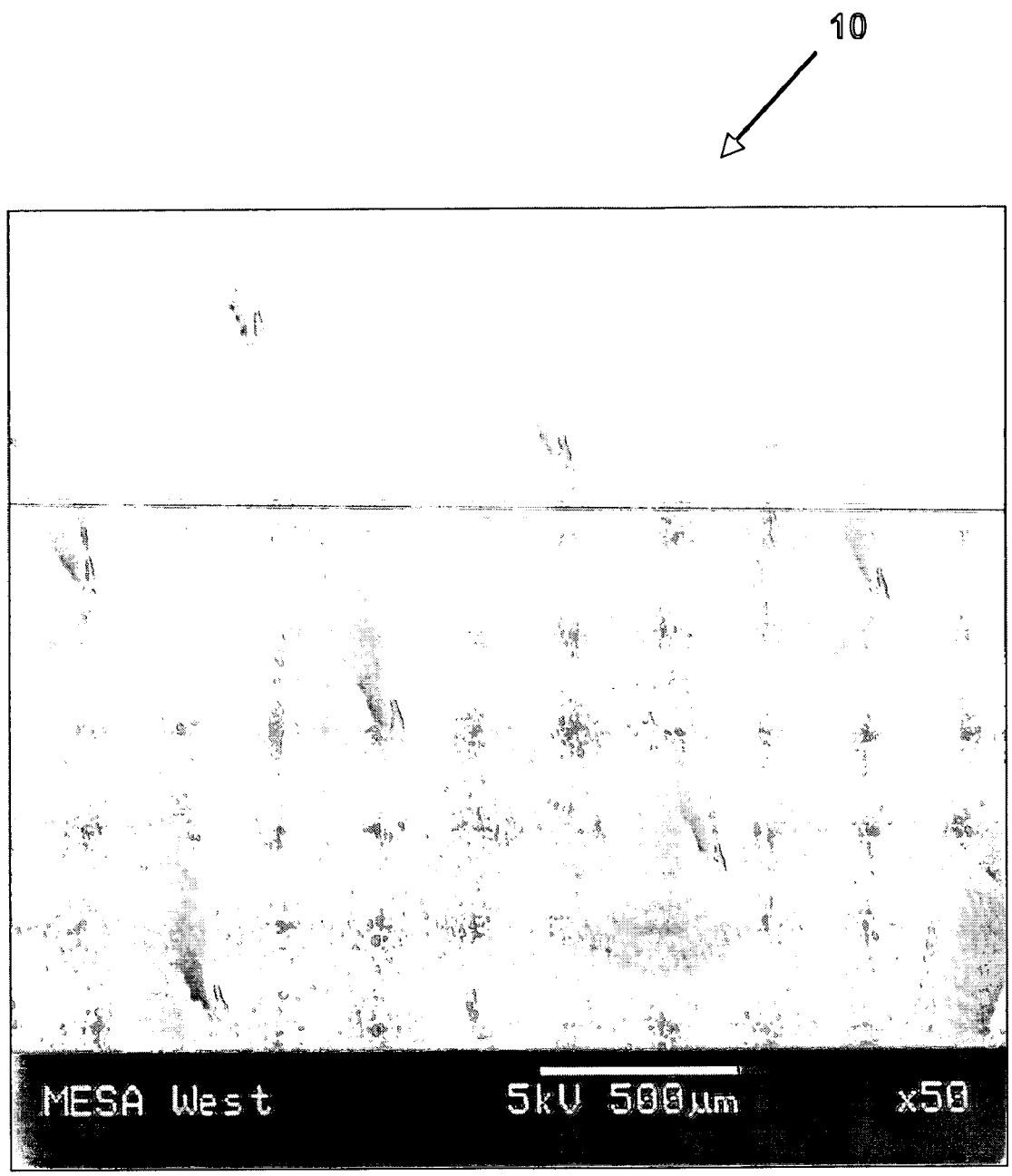
FIG. 5 shows a SEM of a portion of a 4 by 11 rectangular array of the glass hollow microneedles.

In FIG. 5 is shown an SEM of a portion of a 4 by 11 rectangular array 10 of the glass hollow microneedles. The center-to-center spacing between adjacent microneedles is about 1.0 mm.

Figure 6:
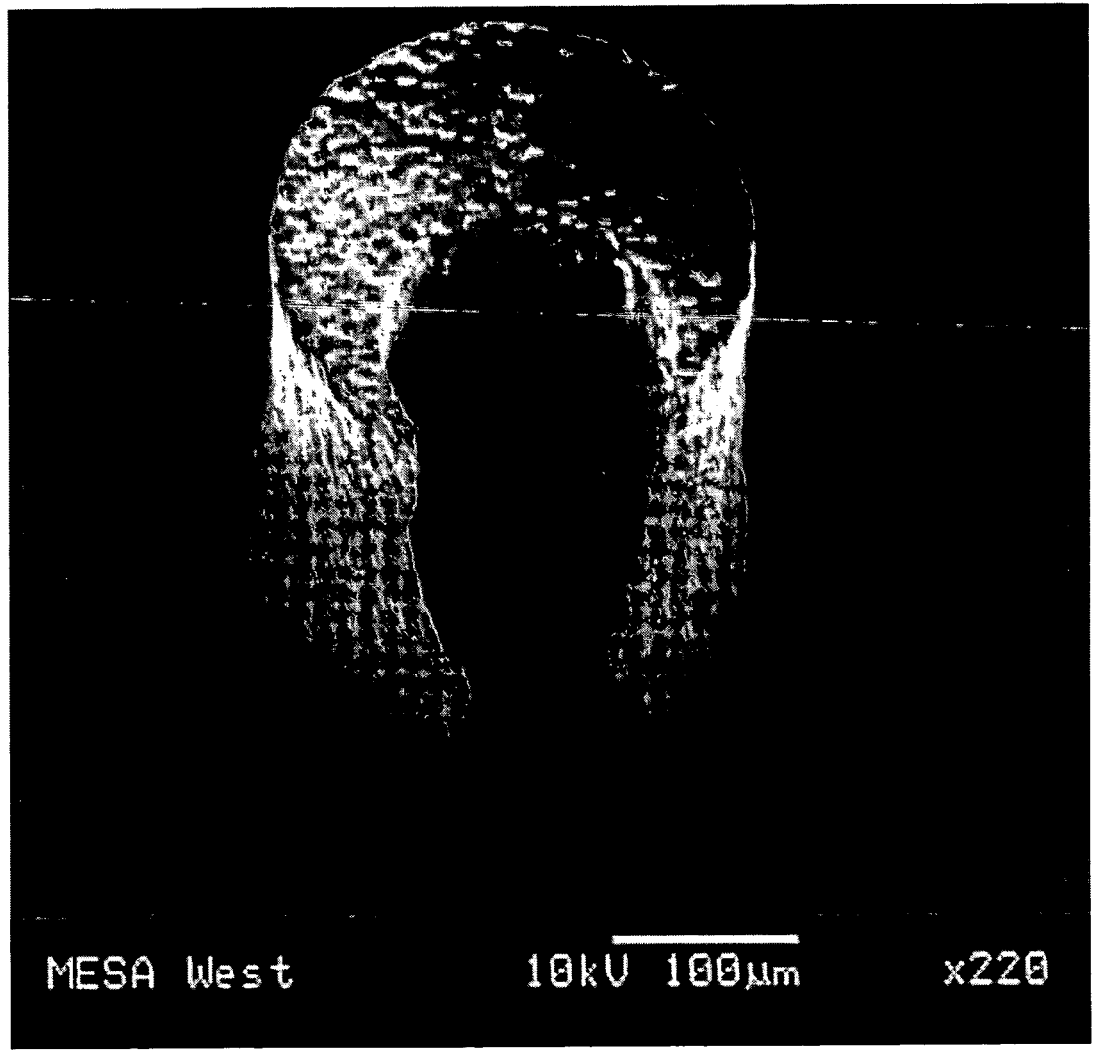
FIG. 6 shows a SEM of a glass hollow microneedle piercing a 100-micron-thickness sheet of aluminum foil.

In FIG. 6 is shown an SEM of a glass hollow microneedle piercing a 100-micron-thickness sheet of aluminum foil. The foil piercing demonstrates the inherent strength of the Foturan® glass microneedles.

An even less expensive method of fabricating the microneedles is to replicate them using a negative mold made from the original glass hollow microneedle array structure. A negative mold can be made by depositing a mold material onto the glass hollow microneedle array. For example, a negative mold of Foturan® microneedles can be made by electroplating a metal (e.g., nickel, copper, or gold) onto a sputtered seed layer deposited on the Foturan® microneedles. After the negative plated mold is created and released from the glass array, a liquid polymer, such as Zeonor 1020R, can be cast into the mold. After the Zeonor 1020R is cooled and solidified, the polymeric hollow microneedle array can be easily peeled off the plated negative mold and the mold can be re-used. Other plastics that can be hot embossed or injection molded, such as polycarbonate, can also be used.

Figure 7A:
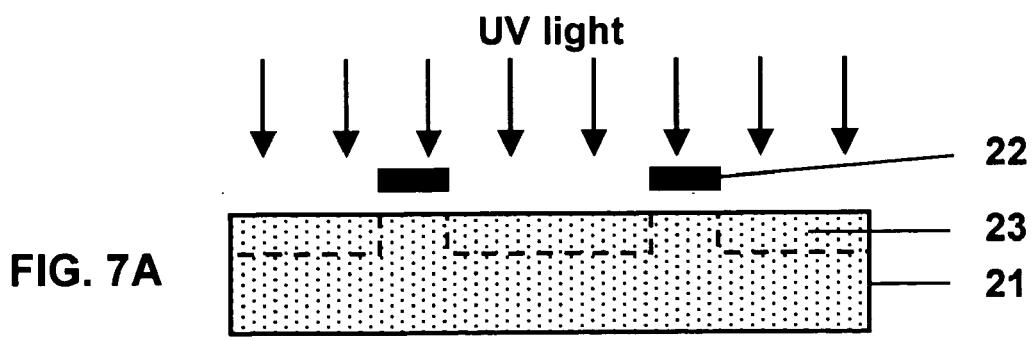
FIGS. 7A–7E show a schematic illustration of a method to fabricate a negative mold of a hollow microneedle array using a photoetchable glass wafer.
Figure 7B:
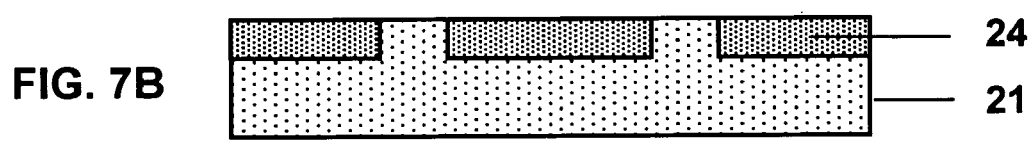
Figure 7C:
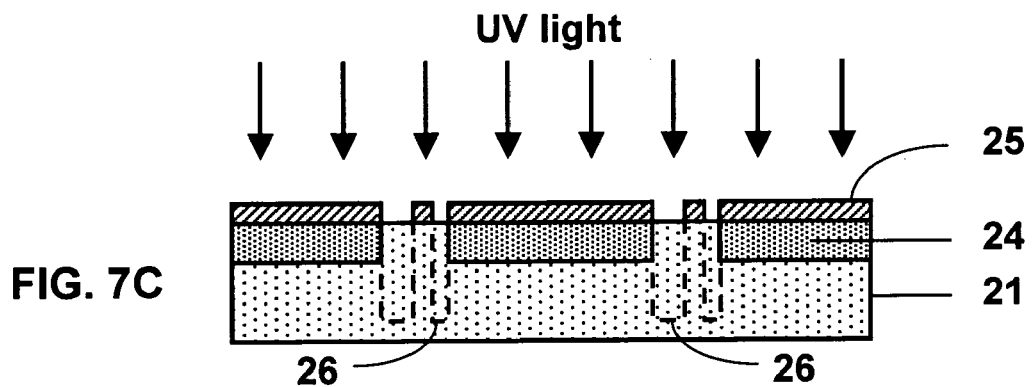
Figure 7D:
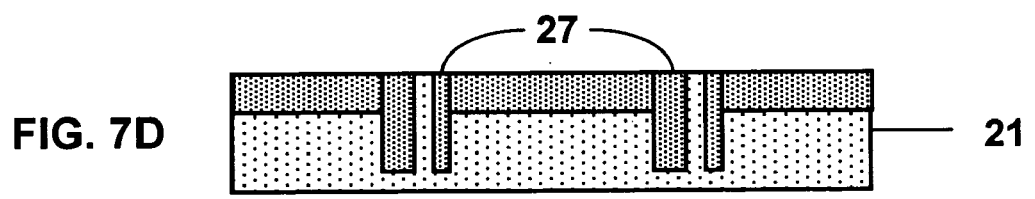
Figure 7E:
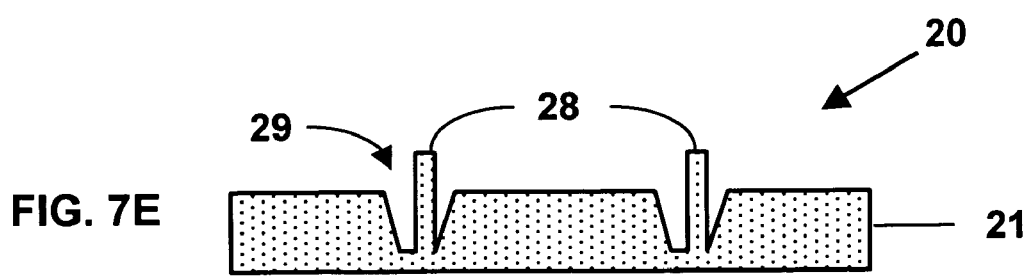

Alternatively, a negative mold can be made directly of the photoetchable glass, as shown in FIGS. 7A–7E. In FIG. 7A, a photoetchable glass wafer 21 is exposed to the deep UV light through a lithography mask 22 to define a latent image 23 of the regions between the microneedles to a depth partially through the thickness of the wafer 21. In FIG. 7B, the exposed wafer is heat-treated to convert the amorphous-phase latent image regions 23 to crystalline-phase image regions 24. In FIG. 7C, a photoresist 25 is patterned onto the front side of the once heat-treated glass wafer using the darkened crystalline image regions 24 as a reference. The photoresist 25 can be patterned to block the areas that will form the bores and regions between the microneedles. The UV exposure can be sufficient to define a latent image 26 of the wall regions of the microneedles to a depth that is greater than the first exposure. In FIG. 7D, the exposed wafer can be heat treated a second time to crystallize the latent image 26 from the second exposure and provide crystallized images 27 of the wall regions of the microneedles. In FIG. 7E, the crystallized image regions 24 and 27 of the glass wafer can be etched to provide a glass negative mold 20. A structural material can then be molded into the negative mold. For example, a polymer can be cast or injection molded, or a metal can be electroplated, into the negative mold. The negative mold can be removed to provide a microneedle array of the structural material. The posts 28 of the negative mold 20 thereby provide the hollow bores and the recessed regions 29 of the negative mold provide the walls of the microneedles.

Alternatively, as described previously, both exposures can be done sequentially to define the latent images of the regions between the microneedles 23 and the wall regions 26. The twice-exposed wafer can then be heat treated to crystallize both latent images 23 and 26 simultaneously to form crystallized images of both the in-between regions 24 and the wall regions 27. The crystallized images can then be etched to form the glass negative mold.

Extraction studies of the Foturan® microneedles for glucose harvesting were made. For these studies, porcine skin was used as a human skin surrogate. The skin was soaked in a deionized water bath for 4 hours to fully saturate the material. Tests were conducted using a Franz diffusion cell. A Franz diffusion cell has fluid on both sides of the porcine skin. Therefore, this method provides a better representation of diffusion through living tissue than having air on one side.

Figure 8:
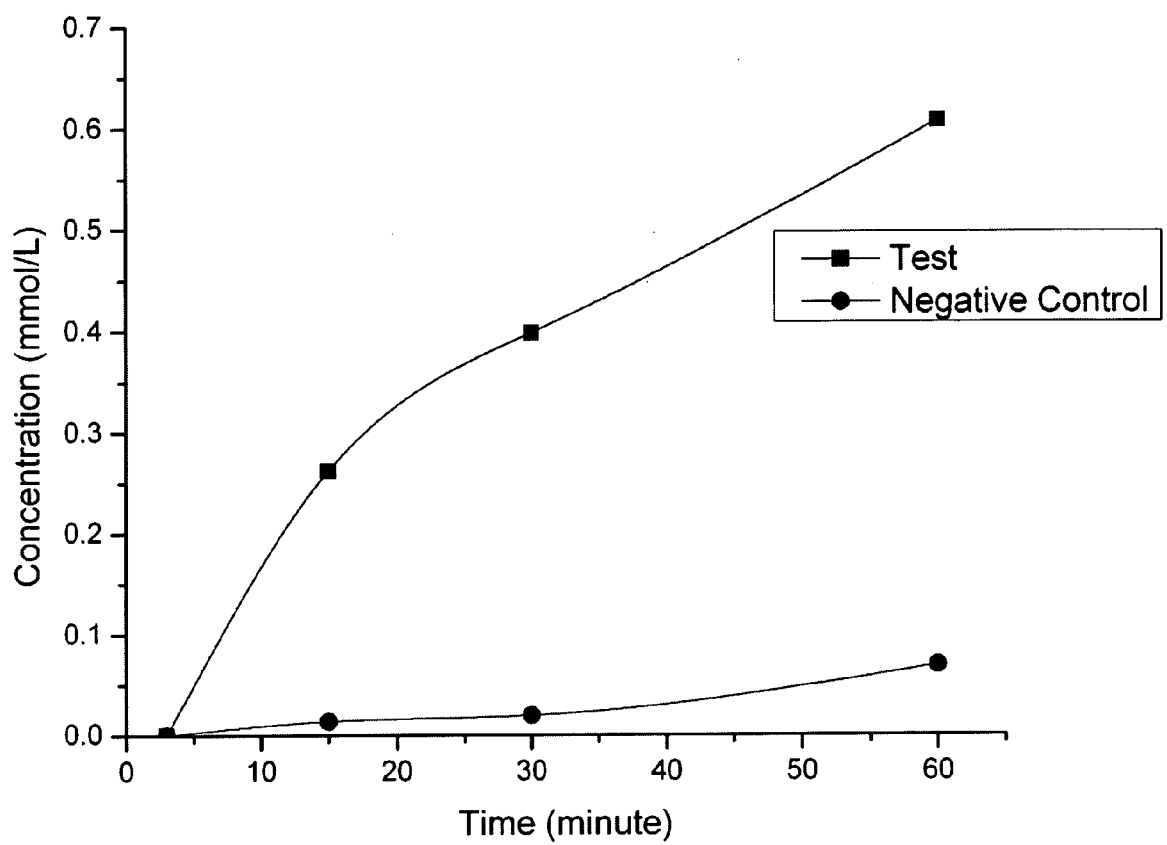
FIG. 8 shows a graph of glucose extraction rates through porcine skin with and without a hollow microneedle array.

In FIG. 8 is shown a graph of glucose extraction rates through porcine skin with and without the glass microneedle array shown in FIG. 5. The flux of glucose transport across the porcine skin, for the negative control, using a 21 mM glucose donor solution, was 0.0012 mM/min/cm$^2$. The flux of glucose transport across the porcine skin, using a 21 mM glucose donor solution, with the microneedles inserted, was 0.609 mM/min/cm$^2$, 500 times greater then the transport without the microneedles in place. Because the open area of the microneedle array is much smaller than the open area of the bare skin, a small change in concentration produces a large change in flux across the microneedle array.

The present invention has been described as a method to fabricate hollow microneedle arrays using photoetchable glass. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method to fabricate a hollow microneedle array, comprising:
   exposing a photoetchable glass wafer to ultraviolet light through a first patterned mask to define a latent image of a bore of at least one hollow microneedle in the glass wafer;
   heating the glass wafer to a temperature in excess of the glass transformation temperature to transform the amorphous material in the exposed latent image of the bore of the at least one microneedle to a crystalline material, thereby providing a crystallized image of the bore of the at least one microneedle in the glass wafer;
   exposing the glass wafer to ultraviolet light through a second patterned mask to define a latent image of the regions between the at least one hollow microneedle, wherein the exposing to define the between regions is performed before or after the exposing to define the bore;
   heating the glass wafer to a temperature in excess of the glass transformation temperature to transform the amorphous material in the exposed latent image of the between regions to a crystalline material, thereby providing an crystallized image of the between regions in the glass wafer; and
   etching the glass wafer in an etchant to remove the crystallized image regions, thereby providing a glass hollow microneedle array comprising the at least one hollow microneedle.

2. The method of claim 1, wherein the photoetchable glass comprises lithium-aluminum-silicate glass containing silver and germanium ions.

3. The method of claim 1, wherein the bore of the at least one hollow microneedle has a cross-sectional dimension of greater than 25 microns.

4. The method of claim 1, wherein the tip of the at least one hollow microneedle has a cross-sectional dimension of greater than 100 microns.

5. The method of claim 1, wherein the height of the at least one hollow microneedle is less than 1 millimeter.

6. The method of claim 1, wherein the etchant comprises hydrofluoric acid.

7. The method of claim 1, wherein the wavelength of the ultraviolet light corresponds to the absorption band of a sensitizing impurity in the photoetchable glass.

8. The method of claim 1, further comprising depositing a mold material onto the glass hollow microneedle array to provide a negative mold, removing the negative mold from the glass hollow microneedle array, casting a liquid polymer into the negative mold, solidifying the polymer in the negative mold, and removing the solidified polymer from the negative mold to provide a polymeric hollow microneedle array.

9. A method to fabricate a hollow microneedle array, comprising:
   exposing a photoetchable glass wafer to ultraviolet light through a first patterned mask to define a latent image of the regions between at least one hollow microneedle in the glass wafer;
   exposing the glass wafer to ultraviolet light through a second patterned mask to define a latent image of a bore of the at least one hollow microneedle,
   heating the glass wafer to a temperature in excess of the glass transformation temperature to transform the amorphous material in the exposed latent image of the between regions and the bore of the at least one microneedle to a crystalline material, thereby providing a crystallized image of the between regions and the bore of the at least one microneedle in the glass wafer; and
   etching the glass wafer in an etchant to remove the crystallized image regions, thereby providing a glass hollow microneedle array comprising the at least one hollow microneedle.

10. The method of claim 9, wherein the photoetchable glass comprises lithium-aluminum-silicate glass containing silver and germanium ions.

11. The method of claim 9, wherein the bore of the at least one hollow microneedle has a cross-sectional dimension of greater than 25 microns.

12. The method of claim 9, wherein the tip of the at least one hollow microneedle has a cross-sectional dimension of greater than 100 microns.

13. The method of claim 9, wherein the height of the at least one hollow microneedle is less than 1 millimeter.

14. A method to fabricate a hollow microneedle array, comprising:
   forming a glass negative mold of the hollow microneedle array, the mold forming comprising:
      exposing a photoetchable glass wafer to ultraviolet light through a first patterned mask to define a latent image of the regions between at least one hollow microneedle in the glass wafer,
      heating the glass wafer to a temperature in excess of the glass transformation temperature to transform the amorphous material in the exposed latent image of the between regions to a crystalline material, thereby providing a crystallized image of the between regions in the glass wafer,
      exposing the glass wafer to ultraviolet light through a second patterned mask to define a latent image of the wall regions of the at least one hollow microneedle, wherein the exposing to define the wall regions is performed before or after the exposing to define the between regions,
      heating the glass wafer to a temperature in excess of the glass transformation temperature to transform the amorphous material in the exposed latent image of the wall regions to a crystalline material, thereby providing an crystallized image of the wall regions in the glass wafer, and
      etching the glass wafer in an etchant to remove the crystallized image regions, thereby providing a glass negative,
   molding a structural material into the glass negative mold; and
   removing the glass negative mold to provide a microneedle array comprising the at least one hollow microneedle of the structural material.

15. The method of claim 14, wherein the photoetchable glass comprises lithium-aluminum-silicate glass containing silver and germanium ions.

16. The method of claim 14, wherein the structural material comprises a polymer.

17. The method of claim 14, wherein the structural material comprises a metal.

18. The method of claim 14, wherein the bore of the at least one microneedle has a cross-sectional dimension of greater than 25 microns.

19. The method of claim 14, wherein the tip of the at least one hollow microneedle has a cross-sectional dimension of greater than 100 microns.

20. The method of claim 14, wherein the height of the at least one hollow microneedle is less than 1 millimeter.

21. The method of claim 14, wherein the etchant comprises hydrofluoric acid.

22. The method of claim 14, wherein the wavelength of the ultraviolet light corresponds to the absorption band of a sensitizing impurity in the photoetchable glass.

23. A method to fabricate a hollow microneedle array, comprising:
   forming a glass negative mold of the hollow microneedle array, the mold forming comprising:
      exposing a photoetchable glass wafer to ultraviolet light through a first patterned mask to define a latent image of the regions between at least one hollow microneedle in the glass wafer,
      exposing the glass wafer to ultraviolet light through a second patterned mask to define a latent image of the wall regions of the at least one hollow microneedle,
      heating the glass wafer to a temperature in excess of the glass transformation temperature to transform the amorphous material in the exposed latent image of the between regions and the wall regions to a crystalline material, thereby providing crystallized images of the between regions and the wall regions in the glass wafer, and
      etching the glass wafer in an etchant to remove the crystallized image regions, thereby providing a glass negative,
   molding a structural material into the glass negative mold; and
   removing the glass negative mold to provide a microneedle array comprising the at least one hollow microneedle of the structural material.

24. The method of claim 23, wherein the photoetchable glass comprises lithium-aluminum-silicate glass containing silver and germanium ions.

25. The method of claim 23, wherein the structural material comprises a polymer.

26. The method of claim 23, wherein the structural material comprises a metal.

27. The method of claim 23 wherein the bore of the at least one microneedle has a cross-sectional dimension of greater than 25 microns.

28. The method of claim 23, wherein the height of the at least one hollow microneedle is less than 1 millimeter.

* * * * *